(12) United States Patent
Ishikawa et al.

(10) Patent No.: US 6,211,284 B1
(45) Date of Patent: Apr. 3, 2001

(54) HIGHLY STORAGE-STABLE ORGANOPOLYSILOXANE COMPOSITION

(75) Inventors: Hiroki Ishikawa; Tsutomu Naganawa; Masaru Ozaki, all of Chiba Prefecture; Isao Ona, Sodegaura, all of (JP)

(73) Assignee: Dow Corning Toray Silicone Co., Tokyo (JP)

( * ) Notice: Subject to any disclaimer, the term of this patent is extended or adjusted under 35 U.S.C. 154(b) by 0 days.

(21) Appl. No.: 09/337,962

(22) Filed: Jun. 22, 1999

(30) Foreign Application Priority Data

Jun. 30, 1998 (JP) .................................. 10-199856

(51) Int. Cl.$^7$ ...................................... C08K 3/20
(52) U.S. Cl. .............. 524/588; 528/29; 528/38; 106/287.11; 8/DIG. 1; 556/445
(58) Field of Search ................ 524/588; 528/29, 528/38; 556/445; 106/287.11; 8/DIG. 1

(56) References Cited

U.S. PATENT DOCUMENTS

| | | | |
|---|---|---|---|
| 4,399,247 | * 8/1983 | Ona et al. | 524/204 |
| 4,450,152 | 5/1984 | Ona et al. | 424/70 |
| 4,459,382 | 7/1984 | Ona et al. | 524/860 |
| 4,921,622 | 5/1990 | Kato et al. | 252/8.9 |
| 4,933,002 | 6/1990 | Petroff et al. | 71/116 |
| 5,036,123 | * 7/1991 | Ozaki et al. | 524/267 |

FOREIGN PATENT DOCUMENTS

| | | |
|---|---|---|
| 52-91994 | 8/1977 | (JP) . |
| 54-142400 | 11/1979 | (JP) . |
| 57-133279 | 8/1982 | (JP) . |
| 59-179885 | 10/1984 | (JP) . |
| 273002 | 3/1990 | (JP) . |
| 5000905 | 1/1993 | (JP) . |
| 2504644 | 12/1997 | (JP) . |

* cited by examiner

Primary Examiner—Margaret G. Moore
(74) Attorney, Agent, or Firm—Charles R. Richard

(57) ABSTRACT

A highly storage-stable organopolysiloxane composition capable of the long-term retention of its surface-modifying activities, such as antistatic and anticlouding activities is disclosed. The composition comprises a first polyoxyalkylene-functional diorganopolysiloxane that is free of amino, carboxyl, and epoxy groups, a second polyoxyalkylene-functional diorganopolysiloxane that contains an amino-functional organic group, and water.

18 Claims, No Drawings

HIGHLY STORAGE-STABLE ORGANOPOLYSILOXANE COMPOSITION

FIELD OF THE INVENTION

This invention relates to highly storage-stable organopolysiloxane compositions. More particularly, this invention relates to a highly storage-stable organopolysiloxane composition that exhibits surface-modifying activities, e.g., antistatic and anticlouding activities, and that can retain these activities long-term.

BACKGROUND OF THE INVENTION

Polyoxyalkylene-functional diorganopolysiloxanes have the ability to impart an excellent smoothness and excellent antistaticity to fiber surfaces, and for this reason are useful as fiber treatment agents (see, for example, U.S. Pat. No. 5,036,123 and Japanese Patent Publications Kokai No's. 52-91994, and 54-142400).

When dissolved or homogeneously dispersed in water, polyoxyalkylene-functional diorganopolysiloxanes cause a substantial decline in the surface tension of the solution. Therefore, polyoxyalkylene-functional diorganopolysiloxanes have also been proposed for use as spreaders for insect repellents, insecticides, and agrochemicals and as penetration assistants for fiber treatment agents (see U.S. Pat. Nos. 4,933,002 and 4,921,622, Japanese Patent Publication (PCT) No. 2-504644, and Japanese Patent Publication Kokai No's. 2-73002, 5-905).

However, when this type of polyoxyalkylene-functional diorganopolysiloxane is dissolved or homogeneously dispersed in water, the polyoxyalkylene group degrades with the passage of time. This timewise degradation results in such problems as a decline in antistatic activity or an increase in the surface tension of the solution and in extreme cases in solution turbidity and/or the production of precipitate.

A polyoxyalkylene-functional diorganopolysiloxane that also carries amino-functional organic groups has been proposed for use as a fiber treatment agent and a hair-control agent (see Japanese Patent Publication Kokai Numbers Sho 57-133279 and 59-179885 and U.S. Pat. Nos. 4,399,247, 4,459,382, and 4,450,152). A drawback to the use of this type of diorganopolysiloxane has been the manifestation of inadequate activities such as anticlouding and antistatic activities.

The object of this invention is to provide a highly storage-stable organopolysiloxane composition that is capable of the long-term retention of its surface-modifying activities, e.g., antistatic and anticlouding activities. It is a further object of this invention to provide the admixture of a special diorganopolysiloxane into a polyoxyalkylene-functional diorganopolysiloxane, wherein the special diorganopolysiloxane induces long-term retention of the surface-modifying activities that such polyoxyalkylene-functional diorganopolysiloxane imparts, such as antistatic and anticlouding activities.

SUMMARY OF THE INVENTION

This invention relates to a highly storage-stable organopolysiloxane composition comprising:
(A) a polyoxyalkylene-functional diorganopolysiloxane that is free of amino, carboxyl, and epoxy groups,
(B) a polyoxyalkylene-functional diorganopolysiloxane containing an amino-functional organic group, and
(C) water.

DETAILED DESCRIPTION OF THE INVENTION

The diorganopolysiloxane (A) used in the present invention is a siloxane that contains at least 1 polyoxyalkylene group per molecule but which is free of amino, carboxyl, and epoxy groups. Diorganopolysiloxane (A) is exemplified by a polymer with the following general formula:

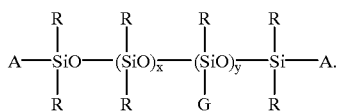

Each R is independently selected from monovalent organic groups excluding amino-functional organic groups, carboxyl-functional organic groups, and epoxy-functional organic groups. R is specifically exemplified by saturated aliphatic hydrocarbon groups such as methyl, ethyl, propyl, butyl, pentyl, hexyl, heptyl, octyl, decyl, and dodecyl; unsaturated aliphatic hydrocarbon groups such as vinyl, allyl, and hexenyl; saturated alicyclic hydrocarbon groups such as cyclopentyl and cyclohexyl; aromatic hydrocarbon groups such as phenyl, tolyl, and naphthyl; halogen-substituted hydrocarbon groups; and methacrylic-functional organic groups. Substituted and unsubstituted monovalent hydrocarbon groups are preferred, and R will most typically be the methyl group.

G represents the polyoxyalkylene group —$(R^1)_a$—O—$(R^2)_b$—$R^3$. $R^1$ represents divalent hydrocarbon groups and is exemplified by alkylene groups such as methylene, ethylene, propylene, and butylene; arylene groups such as —$C_6H_4$—; and alkylenearylene groups such as —$(CH_2)_2C_6H_4$—. $R^2$ represents $C_2$ to $C_4$ oxyalkylene groups and will generally be a —$C_2H_4O$— and/or —$C_3H_6O$— group. $R^2$ may be a single oxyalkylene group or may encompass two or more oxyalkylene groups. When two or more oxyalkylene groups are bonded in $R^2$, their bonding configuration may be that of a random copolymer or a block copolymer. $R^3$ represents the hydrogen atom, monovalent hydrocarbon groups, acyl groups, and the carbamyl group. The monovalent hydrocarbon groups for $R^3$ are exemplified by methyl, ethyl, and propyl. The subscript a is 0 or 1, while b is a number from 1 to 100 and preferably from 5 to 50.

The groups A are selected from R and G, x is a number from 0 to 1,000 and y is a number from 0 to 100. The diorganopolysiloxane (A) is preferably soluble by itself in water or homogeneously dispersible by itself in water.

The diorganopolysiloxane (A) described above is exemplified by the following compounds:

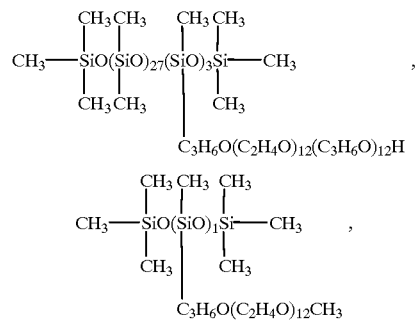

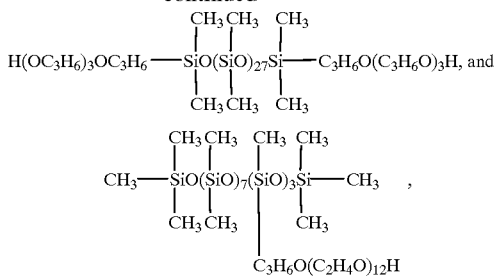

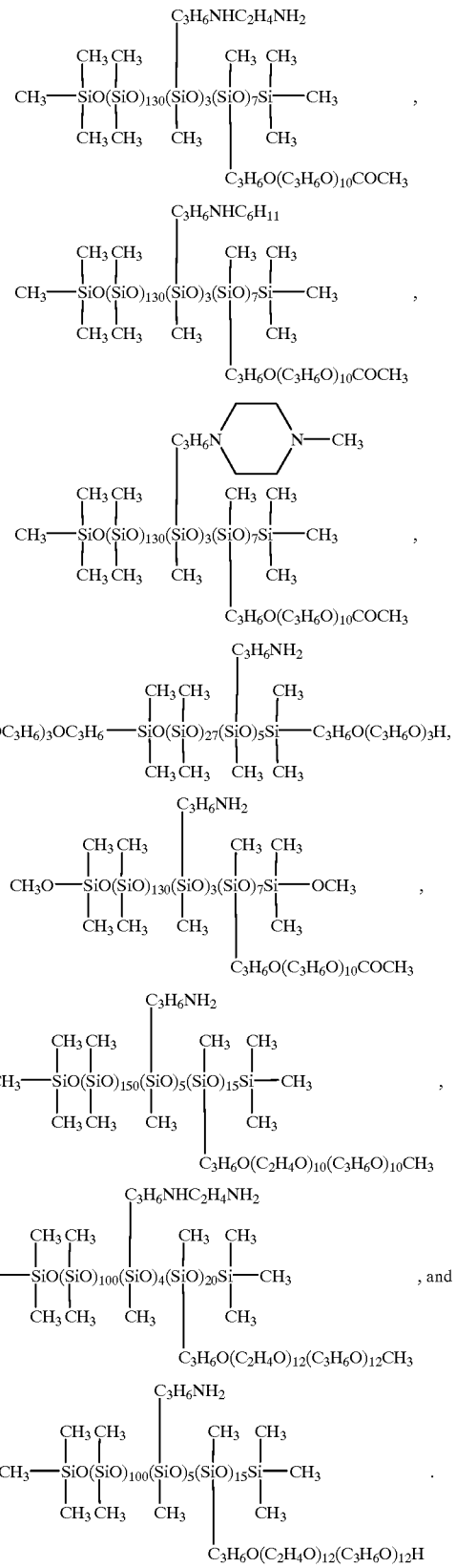

The diorganopolysiloxane (A) can be synthesized by known methods. For example, a polyoxyalkylene-functional diorganopolysiloxane with the formula:

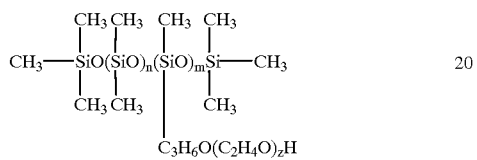

can be synthesized by reacting an SiH containing diorganopolysiloxane with the formula $(CH_3)_3SiO((CH_3)_2SiO)_n$ $((CH_3)HSiO)_mSi(CH_3)_3$, wherein n and m are integers, with the polyoxyethylene allyl ether $CH_2=CHCH_2O(C_2H_4O)_zH$, wherein z is an integer, in the presence of 10 to 20 ppm platinum catalyst.

Each molecule of diorganopolysiloxane (B) must contain at least 1 amino-functional organic group and at least 1 polyoxyalkylene group. This diorganopolysiloxane is exemplified by compounds with the following general formula:

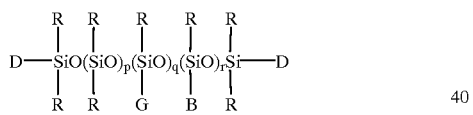

wherein R and G are the same as defined above, while B represents amino-functional organic groups, for example, groups with the formula $—R^1—(NHR^1)_cNR^4{}_2$ and

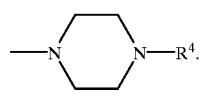

$R^1$ in the preceding formula is defined as above, while $R^4$ is the hydrogen atom or a monovalent hydrocarbon group. The monovalent hydrocarbon groups of $R^4$ can be specifically exemplified by saturated aliphatic hydrocarbon groups such as methyl, ethyl, and propyl and by alicyclic hydrocarbon groups such as cyclopentyl and cyclohexyl. The two groups $R^4$ may be the same or different. The subscript c is 0 or 1. D is selected from R, G, B, the hydroxyl group, and alkoxy groups. The alkoxy groups are exemplified by methoxy, ethoxy, and propoxy, but will generally be methoxy or ethoxy. The subscript p has a value from 0 to 1,000, while q and r are both numbers with values from 0 to 100. The diorganopolysiloxane (B) is preferably soluble by itself in water or homogeneously dispersible by itself in water.

The diorganopolysiloxane (B) is exemplified by the following compounds:

The diorganopolysiloxane (B) can be synthesized by known methods, for example, by base-catalyzed equilibration between a polyoxyalkylene-functional diorganopolysiloxane and a diorganopolysiloxane carrying amino-functional organic groups, or by condensation among a silanol-endblocked diorganopolysiloxane, a polyoxyalkylene-functional alkoxysilane, and an alkoxysilane bearing an amino-functional organic group.

The organopolysiloxane composition of this invention comprises the solution or homogeneous dispersion of diorganopolysiloxane (A) and diorganopolysiloxane (B) in freely selected proportions in water (C). In a preferred embodiment, the blending proportions of the respective components provide an average equivalent weight for the amino-functional organic group (average amino equivalent weight) in (component (A) +component (B)) in the range from 5,000 to 500,000 and more preferably in the range from 10,000 to 100,000. The composition can be prepared, for example, by preliminarily preparing a mixture of components (A) and (B) and dispersing this mixture to homogeneity in water (C) or dissolving it in water (C). Alternatively, components (A) and (B) are each separately dispersed to homogeneity in water (C) or dissolved in water (C) and these two precursors are then intermixed.

The organopolysiloxane composition of this invention has an excellent storage stability. Consequently, this composition is well-suited for application as an antistatic, anticlouding agent, spreader, and penetration assistant. In the case of application as an antistatic, anticlouding agent, or penetration assistant, the composition can be used, for example, by adding the composition to an aqueous solution or water-based emulsion of, various organopolysiloxanes, organic resins, or paraffin. The composition is added in an amount that will provide a diorganopolysiloxane (A) concentration preferably from 0.01 to 5 weight % and more preferably from 0.01 to 1 weight %. In the case of application as a spreader for various water-soluble agrochemicals, insecticides, and insect repellents, the composition is added in an amount that will provide a diorganopolysiloxane (A) concentration preferably from 0.01 to 5 weight % and more preferably from 0.01 to 1 weight %.

Because the organopolysiloxane composition of this invention comprises components (A) to (C), and in particular because it contains the special polyoxyalkylene-functional+amino-containing organic group-functional diorganopolysiloxane (B), this composition is characterized by an excellent storage stability and by the ability to retain its surface-modifying activities (e.g., antistaticity, anticlouding performance) long-term.

EXAMPLES

These examples are intended to illustrate the invention to those skilled in the art and should not be interpreted as limiting the scope of the invention set forth in the claims. In the examples below, parts denotes weight parts.

Example 1

5 parts polyoxyalkylene-functional diorganopolysiloxane (1) with the formula

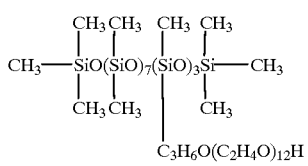

and 0.5 part diorganopolysiloxane (2) with the formula

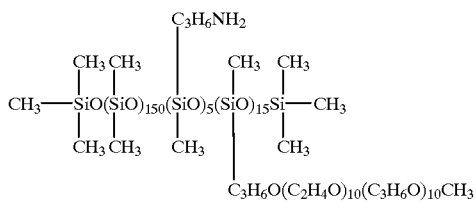

were dissolved in 94.5 parts water to produce an organopolysiloxane composition A (average amino equivalent weight=60,500). The appearance of composition A was monitored for changes over a period of several weeks in order to evaluate its storage stability. These results are reported in Table 1.

A solution was also prepared by diluting organopolysiloxane composition (A) 2-fold with water. 65/35 polyester/cotton white broadcloth was immersed in this solution and then taken out and expressed on a mangle roll so as to provide a 1.5 weight % add-on of polyoxyalkylene-functional diorganopolysiloxane (1). The cloth was then dried until the next day at room temperature and was thereafter heated for 5 minutes at 140° C. The frictional charging voltage was measured on the resulting treated broadcloth and on the untreated broadcloth. After conditioning by standing overnight at 20° C./65% RH, the frictional charging voltage was measured using a Kyodai Kaken rotary static tester. Charging was carried out for 60 seconds at 800 rpm using cotton cloth (unbleached muslin #3) as the friction fabric. The frictional charging voltage was measured using the aqueous solution both immediately after its preparation and after storage for 2 weeks. The frictional charging voltages are reported in Table 2.

Comparative Example 1

An organopolysiloxane composition B was prepared by dissolving 5 parts polyoxyalkylene-functional diorganopolysiloxane (1) with the formula

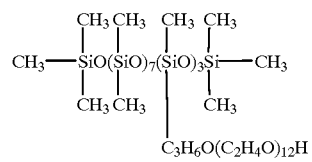

in 95 parts water. The storage stability (change in appearance) and frictional charging voltage were measured on composition B using the procedures described in Example 1. These results are reported in Tables 1 and 2.

TABLE 1

Appearance of the Compositions

| change in appearance | Example 1 | Comparative Example 1 |
|---|---|---|
| immediately after preparation | colorless and transparent | colorless and transparent |
| after 1 week | colorless and transparent | some development of turbidity |

TABLE 1-continued

Appearance of the Compositions

| | Example 1 | Comparative Example 1 |
|---|---|---|
| after 2 weeks | colorless and transparent | white turbidity has appeared |
| after 1 month | colorless and transparent | white turbidity and precipitation have appeared |
| storage stability | very good | poor |

TABLE 2

Frictional Charging Voltages.

| | | Example 1 | | Comparative Example 1 | |
|---|---|---|---|---|---|
| | untreated cloth | immediately after preparation | after 2 weeks | immediately after preparation | after 2 weeks |
| frictional charging voltage | 1850 | 1340 | 1360 | 1310 | 1570 |
| overall evaluation | — | excellent long-term results | | performance deteriorated during long-term storage | |

Example 2

100 parts polyoxyalkylene-functional diorganopolysiloxane (3) with the formula

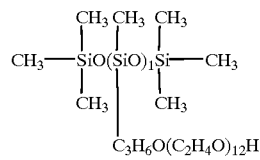

and 5 parts diorganopolysiloxane (4) with the formula

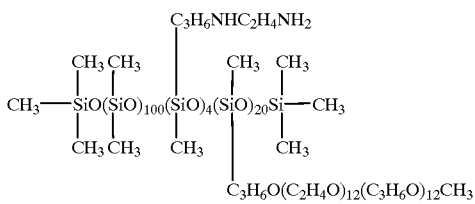

were dissolved in 895 parts water to give an organopolysiloxane composition C (average amino equivalent weight= 88,800). A treatment solution was then prepared by adding composition C to the 1% aqueous solution (2 liters) of an antimicrobial treatment agent with the formula $(C_{18}H_{37}NC_3H_6Si(OCH_3)_3)^+Cl^-$. Composition C was added in a quantity that brought the amount of polyoxyalkylene-functional diorganopolysiloxane (3) to 0.1 weight % of the total final treatment solution. One liter of the resulting treatment solution was stored in a glass bottle. One liter of the remaining treatment solution was transferred to a 50×50×50 cm square vat, and a 30×30 cm specimen of a polypropylene nonwoven fabric primary backing (thickness=35 mm) for nylon tufted carpet was immersed in the treatment solution for 2.5 seconds. After immersion, the fabric was immediately expressed on a mangle roll wringer to an expression ratio of 100%. Using scissors a sample was cut from the antimicrobially-treated polypropylene nonwoven fabric primary backing and the penetration of the treatment bath into the sample was visually evaluated. The same antimicrobial treatment as described above was also carried out using the treatment solution that had been stored for 1 week in the glass bottle, and the penetration of the treatment bath was again evaluated. These results are reported in Table 3.

Comparative Example 2

An organopolysiloxane composition D was prepared by dissolving 100 parts polyoxyalkylene-functional diorganopolysiloxane (3) with the formula

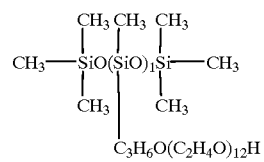

in 900 parts water. Composition D was used as a penetration assistant according to the procedure described in Example 2 to evaluate the penetration performance of the treatment bath. These results are reported in Table 3.

Comparative Example 3

An organopolysiloxane composition E was prepared by dissolving 100 parts polyoxyalkylene-functional diorganopolysiloxane (4) with the formula

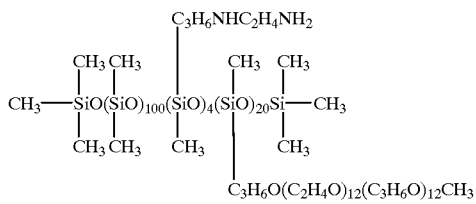

in 900 parts water. Composition E was used as a penetration assistant according to the procedure described in Example 2 to evaluate the penetration performance of the treatment bath. These results are reported in Table 3.

TABLE 3

Penetration Performance

| | Example 2 | Comparative Example 2 | Comparative Example 3 |
|---|---|---|---|
| penetration performance | | | |
| immediately after preparation | the treatment bath had uniformly penetrated even into the core layer of the primary backing | the treatment bath had uniformly penetrated even into the core layer of the primary backing | the core layer of the primary backing remained in its original dry condition and was not wetted; the penetration performance was thus unsatisfactory |

TABLE 3-continued

Penetration Performance

|  | Example 2 | Comparative Example 2 | Comparative Example 3 |
|---|---|---|---|
| after 1 week | the treatment bath had uniformly penetrated even into the core layer of the primary backing | the core layer of the primary backing remained in its original dry condition and was not wetted; the penetration performance was thus unsatisfactory | the core layer of the primary backing remained in its original dry condition and was not wetted; the penetration performance was thus unsatisfactory |
| global evaluation as a penetration assistant | optimal over long-term storage | inadequate storage stability | inadequate penetration performance |

Example 3

1 part polyoxyalkylene-functional diorganopolysiloxane (1) with the formula $$CH_3-SiO(SiO)_7(SiO)_3Si-CH_3$$
with CH$_3$ groups and $C_3H_6O(C_2H_4O)_{12}H$ substituent and 0.1 part diorganopolysiloxane with the formula $$CH_3-SiO(SiO)_{100}(SiO)_5(SiO)_{15}Si-CH_3$$
with CH$_3$ groups, $C_3H_6NH_2$ substituent, and $C_3H_6O(C_2H_4O)_{12}(C_3H_6O)_{12}H$ substituent were dissolved in 98.9 parts water to produce an organopolysiloxane composition F (average amino equivalent weight=60,240). Composition F was divided between 2 glass bottles and one bottle was placed directly in storage. Polypropylene film cut into a narrow strip was dipped for 1 minute in the other portion, and when the film was withdrawn the wetting status of the film surface evaluated. After the film had been dried, it was spread over a beaker in which water was heated to evolve steam. The presence/absence of film clouding was evaluated under these conditions. These results are reported in Table 4.

Comparative Example 4

1 part polyoxyalkylene-functional diorganopolysiloxane (1) with the formula $$CH_3-SiO(SiO)_7(SiO)_3Si-CH_3$$
with CH$_3$ groups and $C_3H_6O(C_2H_4O)_{12}H$ substituent was dissolved in 99 parts water to produce an organopolysiloxane composition G. Composition G was evaluated as in Example 3 for wetting performance and presence/absence of clouding with respect to polypropylene film. These results are reported in Table 4.

TABLE 4

Wetting Performance and Presence/Absence of Clouding

|  |  | Example 3 | Comparative Example 4 |
|---|---|---|---|
| immediately after preparation | wetting performance | the entire film was uniformly wetted | the entire film was uniformly wetted |
|  | presence/absence of clouding | no clouding anywhere on the film | no clouding anywhere on the film |
| after 1 week | wetting performance | the entire film was uniformly wetted | water drops formed in scattered regions of the film |
|  | presence/absence of clouding | no clouding anywhere on the film | clouding occurred in scattered regions of the film |
| long-term storage stability |  | excellent | unsatisfactory |

Example 4

15 g polyoxyalkylene-functional diorganopolysiloxane (1) with the formula $$CH_3-SiO(SiO)_7(SiO)_3Si-CH_3$$
with CH$_3$ groups and $C_3H_6O(C_2H_4O)_{12}H$ substituent and 3 g diorganopolysiloxane (2) with the formula $$CH_3-SiO(SiO)_{150}(SiO)_5(SiO)_{15}Si-CH_3$$
with CH$_3$ groups, $C_3H_6NH_2$ substituent, and $C_3H_6O(C_2H_4O)_{10}(C_3H_6O)_{10}CH_3$ substituent were dissolved and dispersed to homogeneity in 1 liter of water to produce an organopolysiloxane composition (average amino equivalent weight 33,000). Into this was then dispersed 2 g of the antimicrobial agent zinc ethylenebisdithiocarbamate (Dythane from the Du Pont Company (USA)) to prepare an agrochemical spray solution for black rot in onions. This spray solution was divided into two 500-cc samples and one sample was stored for 5 days. The other sample was broadcast over onions (2 months before harvest) using a pressurized sprayer; this sample could be uniformly dispersed and distributed. The sample solution held for 5 days could also be uniformly dispersed and distributed when applied in the same manner.

Comparative Example 5

An agrochemical spray solution was prepared as in Example 4, without the diorganopolysiloxane (2) that was used in Example 4. The sample used immediately after preparation could be uniformly dispersed and distributed when applied as in Example 4. However, a precipitate was found in the spray solution that had been stored for 5 days. Moreover, the stored sample proved to be unusable because this precipitate could not be readily dissolved even the sample was remixed.

We claim:

1. A storage-stable organopolysiloxane composition comprising:
(A) a first polyoxyalkylene-functional diorganopolysiloxane that is free of amino, carboxyl, and epoxy groups,
(B) a second polyoxyalkylene-ftnctional diorganopolysiloxane, with the proviso that each molecule of component (B) comprises at least one polyoxyalkylene group and at least one amino-functional organic group, and
(C) water.

2. The composition of claim 1, wherein (A) has the general formula

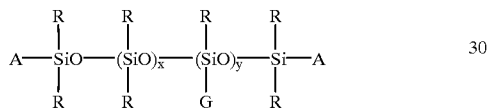

wherein each R is independently a monovalent organic group excluding amino-functional organic groups, carboxyl-functional organic groups, and epoxy-functional organic groups; G represents a polyoxyalkylene group of the formula —$(R^1)_a$—O—$(R^2)_b$—$R^3$, wherein $R^1$ represents a divalent hydrocarbon group, $R^2$ is selected from the group consisting of $C_2$ to $C_4$ oxyalkylene groups and combinations of two or more $C_2$ to $C_4$ oxyalkylene groups, $R^3$ is selected from the group consisting of a hydrogen atom, monovalent hydrocarbon groups, acyl groups, and carbamyl groups, a is 0 or 1, b is a number from 1 to 100; A is selected from the group consisting of R and G; x is a number from 0 to 1,000 and y is a number from 0 to 100.

3. The composition of claim 2, wherein (A) is selected from the group consisting of:

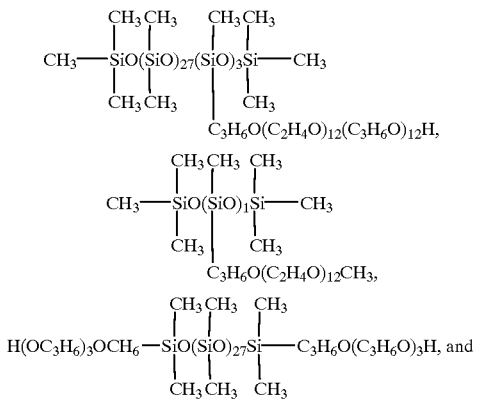

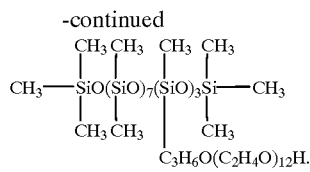

4. The composition of claim 1, wherein (B) has the general formula

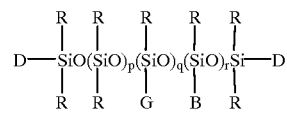

wherein each R is independently selected from monovalent organic groups free of amino-functional organic groups, carboxyl-functional organic groups, and epoxy-functional organic groups; G represents a polyoxyalkylene group of the formula —$(R^1)_a$—O—$(R^2)_b$—$R^3$, wherein $R^1$ represents a divalent hydrocarbon group, $R^2$ is selected from the group consisting of $C_2$ to $C_4$ oxyalkylene groups and combinations of two or more $C_2$ to $C_4$ oxyalkylene groups, $R^3$ is selected from the group consisting of a hydrogen atom, monovalent hydrocarbon groups, acyl groups, and carbamyl groups, a is 0 or 1, b has a value from 1 to 100; B represents an amino-functional organic group selected from the group consisting of —$R^1$—$(NHR^1)_c NR^4_2$ and

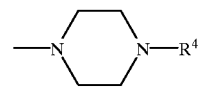

wherein $R^1$ is defined as above, each $R^4$ is independently selected from the group consisting of a hydrogen atom and a monovalent hydrocarbon group; c is 0 or 1; D is selected from R, G, B, a hydroxyl group, and an alkoxy group; p has a value from 0 to 1,000, q has a value from 0 to 100, and r has a value from 1 to 100.

5. The composition of claim 4, wherein (B) is selected from the group consisting of:

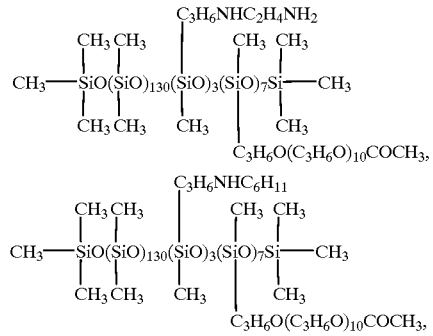

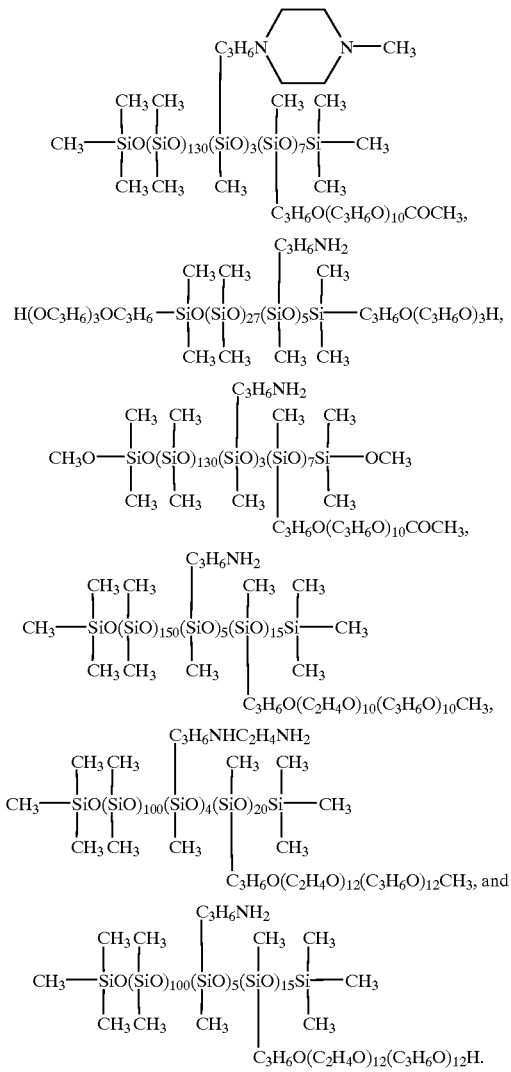

6. The composition of claim 1, wherein (A) and (B) are blended in proportions that provide an average equivalent weight for amino-functional organic groups in the range of 5,000 to 500,000, based on a combined weight of (A) and (B).

7. The composition of claim 6, wherein the range is 10,000 to 100,000.

8. A method for preparing a storage stable organopolysiloxane composition, the method comprising:

1) mixing components (A) and (B), and thereafter 2) combining the product of step 1) with component (C) by a method selected from the group consisting of dispersing to homogeneity and dissolving; wherein component (A) is a first polyoxyalkylene-functional diorganopolysiloxane that is free of amino, carboxyl, and epoxy groups, component (B) is a second polyoxyalkylene-functional diorganopolysiloxane, with the proviso that each molecule of component (B) comprises at least one polyoxyalkylene group and at least one amino-functional organic group, and component (C) is water.

9. The method of claim 8, further comprising 3) adding 0.01 to 5 weight % of the product of step 2) to an aqueous composition selected from the group consisting an aqueous solution and a water-based dispersion, wherein the aqueous composition comprises a compound selected from the group consisting of organopolysiloxanes, organic resins, and paraffin.

10. An organopolysiloxane composition prepared by the method of claim 8.

11. An organopolysiloxane composition prepared by the method of claim 9.

12. A method for preparing a storage stable organopolysiloxane composition, the method comprising 1) combining component (A) with (C) water, 2) combining component (B) with (C) water, and thereafter 3) intermixing the product of step 1) and the product of step 2); wherein component (A) is a first polyoxyalkylene-functional diorganopolysiloxane that is free of amino, carboxyl, and epoxy groups and component (B) is a second polyoxyalkylene-functional diorganopolysiloxane, with the proviso that each molecule of component (B) comprises at least one polyoxyalkylene group and at least one amino-functional organic group.

13. The method of claim 12, further comprising 4) adding 0.01 to 5 weight % of the product of step 3) to an aqueous composition selected from the group consisting an aqueous solution and a water-based dispersion, wherein the aqueous composition comprises a compound selected from the group consisting of organopolysiloxanes, organic resins, and paraffin.

14. The method of claim 9 or 13, wherein the organopolysiloxane composition is selected from the group consisting of an antistatic agent, an anticlouding agent, a spreader, and a penetration assistant.

15. An organopolysiloxane composition prepared by the method of claim 12.

16. An organopolysiloxane composition prepared by the method of claim 13.

17. An organopolysiloxane composition prepared by the method of claim 14.

18. The organopolysiloxane composition of claim 17, wherein the aqueous composition further comprises an antimicrobial treatment agent.

* * * * *